(12) United States Patent
Lee et al.

(10) Patent No.: US 6,489,339 B1
(45) Date of Patent: Dec. 3, 2002

(54) C3A RECEPTOR LIGANDS

(75) Inventors: Dennis Lee, San Mateo, CA (US); William E. Bondinell, Wayne, PA (US); Anthony J. Jurewicz, Royersford, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/762,459

(22) PCT Filed: Aug. 11, 1999

(86) PCT No.: PCT/US99/18256

§ 371 (c)(1),
(2), (4) Date: Feb. 7, 2001

(87) PCT Pub. No.: WO00/09129

PCT Pub. Date: Feb. 24, 2000

Related U.S. Application Data

(60) Provisional application No. 60/096,055, filed on Aug. 11, 1998.

(51) Int. Cl.$^7$ ............... A61K 31/47; A61K 31/198; A61P 19/02; C07D 215/20
(52) U.S. Cl. ............... 514/311; 514/563; 546/175; 562/439
(58) Field of Search ............... 546/175; 562/439; 514/311

(56) References Cited

FOREIGN PATENT DOCUMENTS

FR            2052900         3/1969

Primary Examiner—Robert W. Ramsuer
(74) Attorney, Agent, or Firm—Soma G. Simon; Mary E. McCarthy; Charles M. Kinzig

(57) ABSTRACT

A compound according to Formula (I):

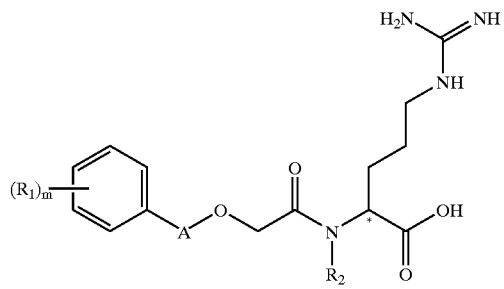

Formula (I)

wherein:

A represents $C_{1-4}$ alkylene, unsubstituted or optionally substituted by $C_{1-4}$ alkyl or aryl; or A forms a 5-8 membered fused aliphatic ring with the adjacent phenyl ring;

m is an integer from 1 to 3;

each $R_1$ is independently selected form the group consisting of halo, $C_{1-4}$ alkyl, methanesulfonyl, alkoxy, nitrile, dimethylamine, methylenedioxy and $CF_3$; and $R_2$ is hydrogen or methyl is provided.

13 Claims, No Drawings

C3A RECEPTOR LIGANDS

This application is a 371 of PCT/US99/182,564 filed Aug. 11, 1999, which claims the benefit of Provisional application No. 60/096,055 filed Aug. 11, 1998.

FIELD OF THE INVENTION

The present invention relates to novel C3A receptor ligands, pharmaceutical compositions containing these compounds and methods of using the present compounds to treat inflammation.

BACKGROUND OF THE INVENTION

Anaphylatoxins are 74–77 amino acid bioactive fragments of C5, C3 and C4 that are generated in vivo during complement activation. Binding of the anaphylatoxins to specific cell surface receptors initiates and maintains the inflammatory process. The fragments are believed to elicit mast cell and basophil degranulation with release of histamine, cytokines and other inflammatory mediators and induce smooth muscle cell contraction. They are potent inflammatory mediators, inducing cellular degranulation, smooth muscle contraction, arachidonic acid metabolism, cytokine release, cellular chemotaxis. See Gerard, C., and Gerard, N. P. (1994) *Annu. Rev. Immunol.* 12, 775–808; Hugli, T. E. (1984) *Springer Semin. Immunopathol.* 7, 193–219; Bitter-Suermann, D. (1988) in *The Complement System*, Ed. by K. Rother & G. Till, Springer Verlag, Heidelberg 367–395.

The present fragments have been implicated in the pathogenesis of a number of inflammatory diseases. See Vogt, W. (1986) *Complement* 3, 177–188; Morgan, B. P. (1994) *European J Clin Investigation* 24, 219–228. Studies have demonstrated the presence of a C3A receptor (C3A-R) on guinea pig platelets, rat mast cells, human neutrophils, eosinophils and platelets (Bitter-Suermann, D. (1988) in The Complement System, Ed. by K. Rother & G. Till, Springer Verlag, Heidelberg 367–395). A single class of high affinity C3A binding sites has been characterized on human neutrophils and differentiated U937 cells (Klos, A., Bank, S., Gietz, C., Bautsch, W., Köhl, J., Burg, M., and Kretzschmar, T (1992) *Biochemistry* 31, 112741–1282). Competition binding and functional desensitization studies are consistent with the presence of a receptor for C3A which is distinct from the C5A-R (Bitter-Suernann, D. (1988) in The Complement System, Ed. by K. Rother & G. Till, Springer Verlag, Heidelberg 367–395; Klos, A., Bank, S., Gietz, C., Bautsch, W., Köhl, J., Burg, M., and Kretzschmar, T. (1992) *Biochemistry* 31, 11274–11282). However, there is evidence that C3A and C4A may bind to the same receptor as the two anaphylatoxins cross desensitize guinea pig ileal tissue (Hugli, T. E. (1984) *Springer Semin. Immunopathol.* 7, 193–219; Bitter-Suermann, D. (1988) in *The Complement System*, Ed. by K Rother & G. Till, Springer Verlag, Heidelberg 367–395), although other investigators using guinea pig macrophages indicate that there may be separate receptors (Murakami, Y., Yamamoto, T., Imamichi, T., Nagasawa, S. (1993) *Immunol. Lett.* 36, 301–304). Functional activity of the C 3A-R is sensitive to pertussis toxin, consistent with the binding site being composed of a GPCR (Klos, A., Bank, S., Gietz, C., Bautsch, W., köhl, J., Burg, M., and Kretzschmar, T. (1992) *Biochemistry* 31, 11274–11282).

A complete understanding of the role of C3A in the pathogenesis of the inflammatory response has been hampered by the lack of the cloned receptor. The present invention provides methods of using and functional characterization of human C3A receptor. This same receptor was recently independently cloned from an HL-60 library by low-stringency screening with a fMetLeuPhe receptor probe and, lacking functional data, claimed to be an orphan receptor (AZ3B,8). Mouse L cells expressing AZ3B failed to bind and respond to the agonists examined, although C3A was not tested (Roglic, A., Prossnitz, E. R., Cavanagh, S. L., Pan, Z, Zou, A. & Ye, R. D. (1996) *Biochimica et Biophysica Acta* 1305, 39–43). The present invention discloses compounds that antagonize C3A receptor function.

Clearly, there is a need for factors that mediate inflammation and their roles in dysfunction and disease. There is a need, therefore, for identification and characterization of compounds which antagonize C3A receptor function, and which can play a role in preventing, ameliorating or correcting dysfunctions or diseases.

Thus, C3A ligands offer a unique approach towards the pharmacotherapy of immune and inflammatory diseases such as rheumatoid arthritis, Alzheimer's disease, psoriasis, gout, multiple sclerosis, systemic lupus erythematosus, glomerulonephritis and adult respiratory distress syndrome.

SUMMARY OF THE INVENTION

The present invention involves compounds represented by Formula (I) hereinbelow and their use as C3A receptor ligands which are useful in the treatment of a variety of diseases associated with complement activation and or increased levels of anaphylatoxins, including but not limited to rheumatoid arthritis, Alzheimer's disease, psoriasis, gout, multiple sclerosis, systemic lupus erythematosus, glomerulonephritis and adult respiratory distress syndrome.

The present invention further provides methods for antagonizing C3A receptors in an animal, including humans, which comprises administering to an animal in need of treatment an effective amount of a compound of Formula (1), indicated hereinbelow.

DETAILED DESCRIPTION OF THE INVENTION

The compounds of the present invention are selected from Formula (I) hereinbelow:

Formula (I)

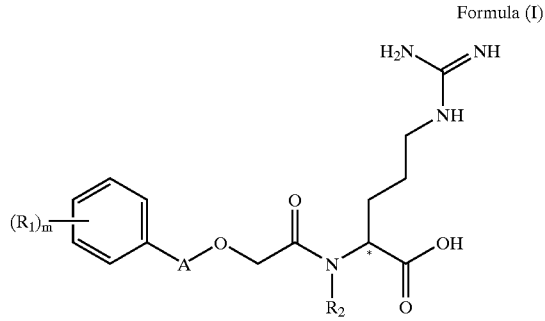

wherein:

A represents $C_{1-4}$ alkylene, unsubstituted or optionally substituted by $C_{1-4}$ alkyl or aryl; or A forms a 5–8 membered fused aliphatic ring with the adjacent phenyl ring;

m is an integer from 1 to 3;

each $R_1$ is independently selected from the group consisting of halo, $C_{1-4}$ alkyl, methanesulfonyl, alkoxy, nitrile, dimethylamine, methylenedioxy and $CF_3$; and $R_2$ is hydrogen or methyl.

Preferably, A represents phenethyl.

Preferably m is 0.

Preferably, $R_1$ represents hydrogen.

Preferably, $R_2$ represents hydrogen.

As used herein, "alkyl" refers to an optionally substituted hydrocarbon group joined together by single carbon-carbon bonds. The alkyl hydrocarbon group may be linear, branched or cyclic, saturated or unsaturated. Preferably, the group is linear. Preferably, the group is unsubstituted. Preferably, the group is saturated.

As used herein "cycloalkyl" refers to 3–7 membered carbocyclic rings.

As used herein "heterocycloalkyl" refers to 4–7 membered heterocyclic rings containing 1 to 2 heteroatoms selected from N, O and S.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted. A preferred aryl group is phenyl.

As used herein "acyl" refers to alkylcarbonyl.

The compounds of the present invention may contain one or more asymmetric carbon atoms and may exist in racemic and optically active forms. All of these compounds and diastereomers are contemplated to be within the scope of the present invention.

Preferred compounds in the present invention include:

1-Naphthyloxyacetylarginine;

1-[7-(4-hydroxyphenylmethyl)naphthyloxy]acetylarginine;

(2,2-Diphenylethoxy)acetylarginine;

(2,2-Diphenylethoxy)acetyl-Nα-methylarginine;

(3-Chlorobenzyloxy)acetylarginine;

2-Naphthyloxyacetylarginine;

(2,3-Dimethylphenoxy)acetylarginine;

8-(Quinolinyloxy)acetylarginine;

6-(Quinolinyloxy)acetylarginine;

2-(1-Bromonaphthyloxy)acetylarginine;

(4-Benzyloxyphenoxy)acetylarginine; and 2-(6-Methoxynaphthyloxy)acetylarginine.

More preferred compounds of the present invention include:

1-Naphthyloxyacetylarginine;

1-[7-(4-hydroxyphenylmethyl)naphthyloxy]acetylarginine;

(2,2-Diphenylethoxy)acetylarginine; and

2-Naphthyloxyacetylarginine.

The most preferred compounds of the present invention include:

1-Naphthyloxyacetylarginine; and (2,2-Diphenylethoxy)acetylarginine.

An especially preferred compound of the present invention is (2,2-Diphenylethoxy)acetylarginine.

The present compounds can also be formulated as pharmaceutically acceptable salts and complexes thereof. Pharmaceutically acceptable salts are non-toxic salts in the amounts and concentrations at which they are administered.

Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, anmmonium, alkylamine, and zinc, when acidic functional groups, such as carboxylic acid or phenol are present.

The present invention provides compounds of Formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

All reagents and solvents were obtained from commercial vendors. Starting materials (e.g., amines and epoxides) were synthesized using standard techniques and procedures. The present invention provides compounds of formula (I) above which can be prepared using standard techniques. An overall strategy for preparing preferred compounds described herein can be carried out as described in this section. The examples which follow illustrate the synthesis of specific compounds. Using the protocols described herein as a model, one of ordinary skill in the art can readily produce other compounds of the present invention.

All reagents and solvents were obtained from commercial vendors. Starting materials were synthesized using standard techniques and procedures.

Aryloxyacetylarginines (eg. 5) can be prepared on solid phase. An appropriately protected arginine derivative such as Fmocarginine(Boc)$_2$ (1) is coupled to chlorotrityl resin with an amine base such as diisopropylamine to give 2. Deprotection, and derivatization with bromoacetic acid yields the intermediate bromoacetamide 3. Reaction of this with arylalcohols under basic conditions such as potassium carbonate or amine bases in DMSO with heating yields the aryloxyacetyl product 4. Deprotection with TFA in the presence of a cation scavenger such as triisopropylsilane, dimethylsulfide, ethanedithiol, anisole, water, or some combination of these yields the cleaved product 5.

Alkyloxy and aryloxy derivatives can be prepared by coupling an appropriately protected arginine derivative such as Fmocarginine(Mtr) (6) to Wang resin. Deprotection and coupling with an alkyloxyacetic acid or aryloxyacetic acid yields the protected resin bound intermediate 7. Finally, deprotection with TFA in the presence of a cation scavenger yields the final product 8.

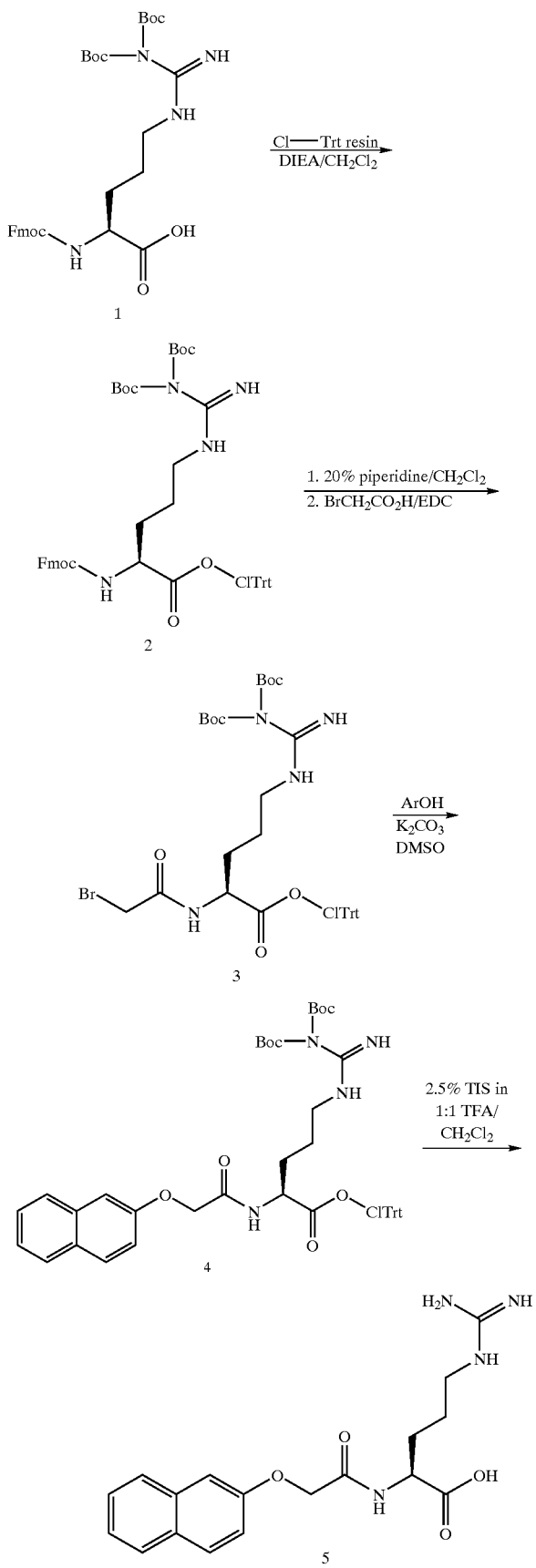
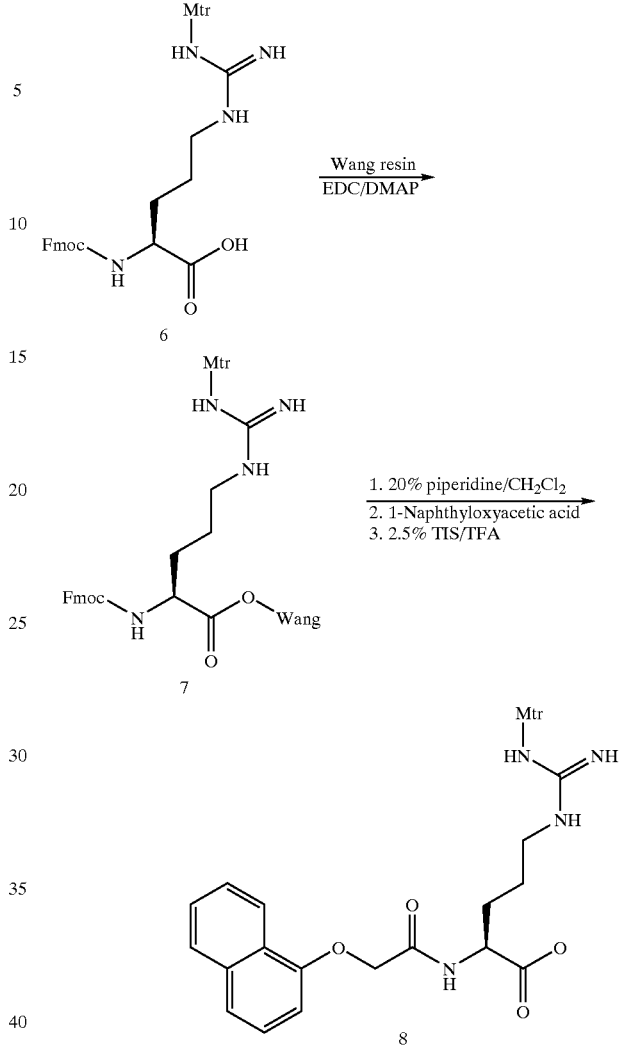

With appropriate manipulation and protection of any chemical functionality, synthesis of the remaining compounds of Formula (I) is accomplished by methods analogous to those above and to those described in the Experimental section.

In order to use a compound of Formula (I) or a pharmaceutically acceptable salt thereof for the treatment of humans and other mammals, it is normally formulated in accordance with standard pharmaceutical practice as a pharmaceutical composition.

The present ligands can be administered by different routes including intravenous, intraperitoneal, subcutaneous, intramuscular, oral, topical, transdermal, or transmucosal administration. For systemic administration, oral administration is preferred. For oral administration, for example, the compounds can be formulated into conventional oral dosage forms such as capsules, tablets and liquid preparations such as syrups, elixirs and concentrated drops.

Alternatively, injection (parenteral administration) may be used, e.g., intramuscular, intravenous, intraperitoneal, and subcutaneous. For injection, the compounds of the invention are formulated in liquid solutions, preferably, in physiologically compatible buffers or solutions, such as saline solution, Hank's solution, or Ringer's solution. In addition, the compounds may be formulated in solid form and redissolved or suspended immediately prior to use. Lyophilized forms can also be produced.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays, rectal suppositories, or vaginal suppositories.

For topical administration, the compounds of the invention can be formulated into ointments, salves, gels, or creams, as is generally known in the art.

The amounts of various calcilytic compounds to be administered can be determined by standard procedures taking into account factors such as the compound IC50, EC50, the biological half-life of the compound, the age, size and weight of the patient, and the disease or disorder associated with the patient. The importance of these and other factors to be considered are known to those of ordinary skill in the art.

Amounts administered also depend on the routes of administration and the degree of oral bioavailability. For example, for compounds with low oral bioavailability, relatively higher doses will have to be administered.

Preferably the composition is in unit dosage form. For oral application, for example, a tablet, or capsule may be administered, for nasal application, a metered aerosol dose may be administered, for transdermal application, a topical formulation or patch may be administered and for transmucosal delivery, a buccal patch may be administered. In each case, dosing is such that the patient may administer a single dose.

Each dosage unit for oral administration contains suitably from 0.01 to 500 mg/Kg, and preferably from 0.1 to 50 mg/Kg, of a compound of Formula (I) or a pharmaceutically acceptable salt thereof, calculated as the free base. The daily dosage for parenteral, nasal, oral inhalation, transmucosal or transdermal routes contains suitably from 0.01 mg to 100 mg/Kg, of a compound of Formula(I). A topical formulation contains suitably 0.01 to 5.0% of a compound of Formula (I). The active ingredient may be administered from 1 to 6 times per day, preferably once, sufficient to exhibit the desired activity, as is readily apparent to one skilled in the art.

As used herein, "treatment" of a disease includes, but is not limited to prevention, retardation and prophylaxis of the disease.

Diseases and disorders which might be treated or prevented, include immune and inflammation-related diseases or disorders such as rheumatoid arthritis, Alzheimer's disease, psoriasis, gout, multiple sclerosis, systemic lupus erythematosus, glomerulonephritis and adult respiratory distress syndrome.

Composition of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose.

Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

No unacceptable toxological effects are expected when compounds of the present invention are administered in accordance with the present invention.

The biological activity of the compounds of Formula (I) are demonstrated by the tests indicated hereinbelow.

Stable Expression of C3A Receptor in RBL-2H3 Cells

To prepare C3A receptor for expression in mammalian cells, a 1.6 kb cDNA fragment was obtained by PCR amplification that encompassed the entire C3A Receptor open reading frame. This fragment was subcloned into KpnI/Hind III sites of the mammalian expression vector, pCDN (Aiyar, N., et al (1994) *Mol. Cell. Bio.* 131, 75–86). Oligonucleotide primers used for PCR amplification were 5'-GA AGT GGT ACC <u>ATG</u> GCG TC-3' and 5'-GC TCC AAG CTT <u>TCA</u> CAC AGT TG-3' (the translation start and stop codons are underlined). RBL-2H3 cells were electroporated with C3A in the pCDN mammalian expression vector (Aiyar, N., et al (1994) *Mol. Cell. Bio.* 131, 75–86), exactly as described (DeMartino, J. A., et al (1994) *J. Biol. Chem.* 269, 14446–14450). Individual G418 resistant (400 $\mu$g/ml) colonies were isolated and expanded. Clonal cell lines expressing C3A receptor, as determined by ability of the cell line to respond to C3A in a calcium mobilization assay, were chosen for further functional and binding studies.

Preparation of Membranes

RBL-2H3 cells expressing the human C3A receptor (hC3AR) were cultured to confluency at 37° C. in a humidified incubator with 5% CO2/95% air, in Earls MEM supplemented with non-essential amino acids, 10% fetal calf serum and 400 $\mu$g/ml G418. Although this cell line is normally adherent, nonadherent cells are always present in cultures. The nonadherent cells were adapted to grow in suspension. Nonadherent cells from three T-150 flasks were centrifuged at 1,000×g for 10 min and resuspended in 50-ml of the above medium in a 250 ml shake flask and over 7–10 days the cells were expanded to 2.5l in a spinner flask. Cells were harvested by centrifugation, 1,000×g for 10 min at 4° C., and membranes were isolated using a modification of the procedure of Ross et al., (1977). Briefly, the cell pellet was washed with PBS and resuspended in 30 ml of hypotonic membrane buffer (20 mM Tris, pH 7.5, 2 mM $MgCl_2$, 0.1 mM EDTA, 1 mM DTT, 1 mM phenylmethylsulfonyl fluoride, 1 $\mu$M leupeptin, 1 $\mu$M pepstatin A) and incubated on ice for 5 min. The cell suspension was homogenized in 40 ml Dounce homogenizer and centrifuged at 1,000×g for 15 min to remove nuclei and cellular debris. Cell membranes were pelleted at 100,000×g for 30 min at 4° C. Membranes were resuspended in membrane buffer with 10% sucrose and layered over membrane buffer with 40% sucrose and centrifuged at 100,000×g for 90 min at 4° C. Membranes at the interface were isolated and collected by centrifugation at 100,000×g for 30 min. The membrane pellet was resuspended in 5.0 ml of membrane buffer and aliquots stored at −80° C. Protein concentration was quantified using the BCA protein assay reagent (Pierce, Rockford, Ill.).

Scintillation Proximity Assay

All assays are performed in a 96-well micro-titre plate format. The 96-well plates (1450-401) are obtained from Wallac, Turku, Finland. Human anaphylatoxin C3A was obtained from Advanced Research Technologies, San Diego, Calif. with Bolton-Hunter custom iodination being performed by NEN Research Products, Boston, Mass. with specific activity of 2200 Ci/mmol. Wheatgerm agglutinin SPA (Scintillation Proximity Assay) beads were obtained from Amersham Corp., Arlington Heights, Ill. The binding buffer consists of 20 mM Bis-Trispropane, 25 mM NaCl, 1 mM $MgSO_4$, 0.1 mM EDTA at pH 8.0. Each reaction mixture contains: 125I C3A (25 pM, obtained from NEN, Boston Mass.), wheatgerm agglutinin SPA beads (0.1 mg), 0.35 $\mu$gs of RBL-2H3 C3A receptor membranes (this may vary with quality of membrane preparation), 23 ug/ml BSA and 0.03% CHAPS in binding buffer.

The membranes were prebound to SPA beads for 30 minutes on ice while shaking. The mixture of membranes and beads were centrifuged for three minutes at 2000 rpm. The supernatant was removed and the pellet was resuspended to original volume in binding buffer with 50 ug/mL BSA. Samples of interest were dissolved in neat DMSO to yield a 20× solution followed by a 1:1 mixture with $H_2O$ to yield a 10×, 50% DMSO working solution. The order of addition was 10 uLs sample, 45 uLs membrane bound SPA beads followed by 45 uLs of radiolabled ligand in binding buffer containing 0.06% CHAPS. The plates were covered with plate sealers from Dynex Technologies, Inc, and shaken for 20 minutes and incubated an additional 40 minutes at room temperature. The plates were then centrifuged for three minutes at 2000 rpm followed by counting on the Wallac 1450 Micro Beta Plus Liquid Scintillation counter.

Calcium Functional Assays

7TM receptors which are expressed in HEK 293 cells have been shown to be coupled functionally to activation of PLC and calcium mobilization and/or cAMP stimulation or inhibition. Basal calcium levels in the HEK 293 cells in receptor-transfected or vector control cells were observed to be in the normal, 100 nM to 200 nM, range. HEK 293 cells expressing recombinant receptors are loaded with fura 2 and in a single day >150 selected ligands or tissue/cell extracts are evaluated for agonist induced calcium mobilization. Agonists presenting a calcium transient are tested in vector control cells to determine if the response is unique to the transfected cells expressing receptor.

Calcium Mobilization: C3a-induced Response in RBL-2H3 cells carrying C3a receptor:

Bioassays:

The functional activity of an antagonist of the C3a receptor is demonstrated using the C3a-induced $Ca^{2+}$ mobilization in RBL-2H3 cells stably expressing C3a (RBL-2H3-C3a).

RBL-2H3-C3a Cell Culture Conditions:

RBL-2H3-C3a cells were cultured to near confluence in T-150 flasks at 37°C. in a humidified incubator with 5% $CO_2$/95% air in Earls MEM with Earls salts (Gibco) supplemented with non-essential amino acids and L-glutamate, with 10% fetal calf serum (Gibco) and 400 ug/ml G418 (Gibco).

Fluorescent Measurements-Calcium Mobilization:

The functional assay used to assess antagonist activity of compounds was C3a-induced calcium mobilization in intact RBL-2H3-C3a cells. Cells were washed with 50 mM Tris, pH 7.4 containing 1 mM EDTA. The $[Ca^{2+}]_i$ was estimated with the calcium fluorescent probe-fura 2 (Grynkiewicz, et al., J. Biol. Chem., 1985, 260, 3440–3450). The media was aspirated from RBL-2H3-C3a cells that were near confluence in T-150 flasks then 40 ml in Krebs Ringer Hensilet containing 0.1% BSA, 1.1 mM $MgCl_2$ and 5 mM HEPES, pH 7.4 (buffer A) was added. The diacetoxymethoxy ester of fura 2 (fura 2/AM) was added at a concentration of 2 $\mu$M and incubated for 45 min at 37° C. Buffer A was aspirated off the RBL-2H3-C3a cells and 40 ml of Buffer A was added to the cells and incubated for an additional 20 min to allow complete hydrolysis of the entrapped ester. Buffer A was aspirated and cells covered with ~5 ml of Delbeccos Phosphate Buffered Saline with 1 mM EDTA (no calcium or magnesium) for 5 min at 37° C. Buffer is aspirated off and 40 ml of buffer A added to the cells which were then mechanically detached from the flasks. RBL-2H3-C3a cells were maintained at room temperature until used in the fluorescent assay which was performed within 3 hours.

The fluorescence of fura 2 containing cells was measured with a fluorometer designed by the Johnson Foundation Biomedical Instrumentation Group. The fluorometer was equipped with a temperature control and a magnetic stirrer under the cuvette holder. Wavelengths were set at 340 nm (10 nm band width) for excitation and 510 nm (20 nm band width) for emission. All experiments were performed at 37° C. with constant stirring. For compound studies, fura 2 loaded cells were centrifuged and resuspended in buffer A containing 1 mM $CaCl_2$ minus BSA at $10^6$ cells/mL. For assessment of agonist activity, a 2 mL aliquot of RBL-2H3-C3a cells was added to a cuvette and warmed in a water bath to 37° C. The 1 $cm^2$ cuvette was transferred to the fluorometer and fluorescence was recorded for 15 seconds to ensure a stable baseline before addition of compound. Fluorescence was recorded continuously for up to 2 mins after addition of compounds to monitor for the presence of any agonist activity.

For antagonist studies, varying concentrations of compounds or vehicle were added to the fura 2 loaded RBL-2H3-C3a cells and monitored for 1 min to ensure that there was no change in baseline fluorescence followed by the addition of 1 nM C3a. The maximal $[Ca^{2+}]$/fura 2 fluorescence was then determined for each sample. The $[Ca^{2+}]_i$ was calculated using the following formula:

$$[Ca^{2+}]_i = 224 \text{ (nM)} \frac{F - F_{min}}{F_{max} - F}$$

The percent of maximal C3a (1 nM) induced $[Ca^{2+}]_i$ was determined for each concentration of compound and the IC50 defined as the concentration of test compound that inhibits 50% of the maximal C3a response. Concentration response curves (5–7 concentrations) were run.

High-Throughput-Screening-Calcium Assay:

The calcium assay described above was converted to a high-throughput-screen (HTS) with the use of a 96 well Fluorescent Imaging Plate Reader (FLIPR) from Biomolecular Devices. This technology allows the measurement of the intracellular calcium mobilization in cells attached to the bottom of a 96 well plate.

For this procedure, cells were obtained from the T-150 flasks as described above. The cells were plated into the 96 well plate at 30,000 cells/well. With incubation in a humidified environment in a cell incubator at 37° C. for 18–24 hours, the cells attached to the bottom surface of the 96 well plate.

The FLIPR works best with the visible wavelength calcium indicators, Fluo-3 and Calcium green-1. Both of these dyes have been used successfully for the HTS assay, but Fluo-3 was generally used. Typically 4 uM Fluo-3 was loaded into the cells for 1 hr at 37° C. in cell media without fetal calf serum and with 1.5 mM sulfinpyrazone to inhibit dye release from the cells. The media is aspirated from the cells and fresh media was added for 10 min at 37° C. to allow hydrolysis of the dye and remove extracellular dye. The media was aspirated and replaced with KRH buffer (buffer A above). After 10 min at 37° C. the cells were placed in FLIPR apparatus for analysis.

FLIPR has 3–96 well plates. In addition to the plate with dye loaded cells, there is a plate containing varying concentrations of compound or vehicle and the third plate has the agonist at varying concentrations to establish agonist potency or a single concentration, e.g., 1 nM of C3a for antagonist activity. For antagonist studies, FLIPR obtains a baseline fluorescence for ~30 sec, then it adds the compounds to all 96 wells simultaneously and begins to monitor changes in intracellular $Ca^{2+}$. After 2 min, the contents or the agonist plate is added to the cells. The maximal $Ca^{2+}$ response (in optical units) for 1 nM C3a in the presence of vehicle (100%) or the various concentrations of compound is determined. Inhibition curves were generated essentially as described for the single cuvette Fura-2 assay described above.

The following examples are illustrative of the present invention but not intended to be limiting in any way.

EXAMPLE 1

(2-Naphthyloxy)acetylarginine a) Fmocarginine(Boc)$_2$ Chlorotrityl Resin

To a mixture of Fmocarginine(Boc), (12.2 g) and chlorotrityl resin (1.8 g, loading=1.05 mmol/g) in 30 mL of $CH_2Cl_2$ was added diisopropylethylamine (700 uL). The mixture was agitated for 16 h and the liquid phase was drained. The resulting resin was washed with N-methylpyrollidine (2×) and $CH_2Cl_2$ (3×) to yield 2.2 g of product.

b) Bromoacetylarginine(Boc)$_2$ Chlorotrityl Resin

To Fmocarginine(Boc)$_2$_Chlorotrityl resin (2.2 g) was added 20% piperidine in $CH_2Cl_2$ (50 mL). The mixture was agitated for 1 h and the liquid phase was drained. The resulting resin was washed with $CH_2Cl_2$ (5×).

The resin was swelled in DMF and to the mixture was added bromoacetic acid (5.8 g) and EDC (2.9 g). The solution was agitated for 4 h and the liquid phase was drained. The resulting resin was washed with N-methylpyrollidine (2×) and $CH_2Cl_2$ (4×).

c) 2-Naphthyloxyacetylarginine(Boc)$_2$Chlorotrityl Resin

To bromoacetylarginine(Boc)$_2$_Chlorotrityl resin (75 mg) in 1.5 mL of DMSO was added 2-naphthol (10 eq) and potassium carbonate (100 mg), and the mixture was shaken at 80° for 4 h. The liquid phase was drained and the resin was washed with N-methylpyrollidine (2×) and $CH_2Cl_2$ (3×).

d) 2-Naphthyloxyacetylarginine

2-Naphthyloxyacetylarginine(Boc)$_2$_Chlorotrityl resin (~75 mg) was agitated in 5 mL of 2.5% triisopropylsilane (TIS) in 1:1 $CH_2Cl_2$/TFA for 2 h. The liquid phase was collected in a flask and the solvent was evaporated under reduced pressure. The residue was dissolved in 1 mL of TFA and added to 7 mL of ether to precipitate out the product as a white solid. The heterogeneous mixture was centrifuged and the solvent was decanted. Ether was added to the resulting solid, the mixture centrifuged and the solvent decanted again. The product was dried under vacuum. ES(+) MS m/e=359.2 (M+H).

EXAMPLE 2

1-Naphthyloxyacetylarginine a) Fmocarginine(Mtr) Wang

To Wang resin (10 g, 12 mmol) in $CH_2Cl_2$ (250 mL) was added Fmocarginine(Mtr) (9.31 g, 15 mmol), EDC (2.93 g, 15 mmol), and DMAP (1.44 g, 12 mmol). Argon was bubbled through it to agitate the reaction overnight. The slurry was filtered and washed with $CH_2Cl_2$ for 30 min. Solvent was drained off, and a second washing was performed at the same condition for 5 h. Then the slurry was filtered, washed with $CH_2Cl_2$ (1×), NMP (3×), $CH_2Cl_2$ (3×), and dried under high vaccum for 24 h to give Fmocarginine (Mtr) Wang. Nitrogen analysis indicated a substitution of 0.73 mmol/g.

b) 1-Naphthyloxyacetylarginine(Mtr) Wang

Deprotection of Fmocarginine(Mtr) Wang was effected with 20% piperidine in $CH_2Cl_2$ (200 mL) for 30 min. The solution phase was drained, and a second round of deprotection was carried out for 15 min. The solution was drained, and the resin was washed with $CH_2Cl_2$ (5×) to afford arginine(Mtr) Wang. To this intermediate (2 g, 2.4 mmol) in DMF (20 mL) was added 1-naphthyloxyacetic acid (2.43 g, 12 mmol), EDC (2.3 g, 12 mmol), and HOBT (1.62 mmol, 12 mmol). After overnight shaking, the slurry was filtered, and washed with DMF (2×)/$CH_2Cl_2$ (6×).

c) 1-Naphthyloxyacetylarginine

To 1-naphthyloxyacetylarginine(Mtr) Wang was added 2.5% TIS in TFA (45 mL). After shaking for 5 h, the solvent was evaporated under reduced pressure. The residue was purified by preparative HPLC to afford the title compound. ES(+) MS m/e=359.4 (M+H).

EXAMPLE 3

1-[7-(4-Hydroxyphenylmethyl)Naphthyloxy]acetylarginine

The title compound was obtained as a byproduct in example 2c). ES(+) MS m/e=465.4 (M+H).

EXAMPLE 4

(2,2-Diphenylethoxy)acetylarginine a) Fmocaroinine(Boc)$_2$ Wang

To Fmocarginine(Boc)$_2$(1.8 g, 3 mmol) and Wang resin (2 g, 2 mmol) in $CH_2Cl_2$ (40 mL) was added EDC (573 mg, 3 mmol) and DMAP (244 mg, 2 mmol). The mixture was shaken overnight and washed with DMF (2×)/$CH_2Cl_2$ (6×).

b) (2,2-Diphenylethoxy)acetic Acid

To 2,2-diphenylethanol (1 g) in DMF (10 mL) was added 60% sodium hydride (350 mg) at 0° C. under Ar. The solution was stirred for 10 min, and t-butyl bromoacetate (888 uL) was added, and the solution was warmed to RT. After stirring 30 min, the reaction was quenched with water (20 mL), and the aqueous solution was extracted with ether (25 mL). The organic layer was washed with water (20 mL) and brine (20 mL). The organic solution was dried ($MgSO_4$), and silica gel flash chromatography (3% ethyl acetate/hexanes) yielded t-butyl (2,2-diphenylethoxy)acetate. The intermediate was treated with 25% $TFA/CH_2Cl_2$ for 1 h. The solvent was removed, and traces of TFA was removed by azeotroping with toluene to yield the title compound. 1H NMR ($CDCl_3$) δ 7.1–7.4 (m, 10H), 4.32 (t, J=8.4 Hz, 1H), 4.0–4.1 (m, 4H).

c) (2,2-Diphenylethoxc)acetylarginine(Boc)$_2$ Wang

Fmocarginine(Boc)$_2$_Wang (200 mg) was treated with 20% piperidine in $CH_2Cl_2$ (5 mL) for 30 min. The solvent was drained and the resin was washed with $CH_2Cl_2$ (6×). To the resin in DMF (3.5 mL) was added (2,2-diphenylethoxy)acetic acid (92 mg), EDC (69 mg), and HOBT (49 mg), and the mixture was shaken overnight. The solution was drained, and the resin was washed with DMF (2×)/$CH_2Cl_2$ (6×).

d) (2,2-Diphenylethoxn)acetylarginine

The resin was treated with a solution of 2.5% TIS in 1:1 $TFA/CH_2Cl_2$ for 90 min. The cleavage solution was collected, the solvent removed under reduced pressure, and traces of TFA were removed by azeotroping with toluene. The residue was washed with hexanes (2×) to yield the title compound. ES(+) MS m/e=413.3 (M+H).

EXAMPLE 5

(3-Chlorobenzyloxy)acetylarginine

The tide compound was prepared according to the procedure of Example 4 except substituting 3-chorobenzylalcohol for 2,2-diphenylethanol. ES(+) MS m/e=357.2 (M+H).

EXAMPLE 6

(2,2-Diphenylethoxy)acetyl-Nα-methylarginine a) Nα-methylarginine(Mtr)OMe TFA Salt To Boc-Nα-methylarginine(Mtr) (1 g, 2 mmol) in dry THF (50 mL) at 0° C. is added diazomethane (5 mmol) in ether (10 mL). The solution was stirred for 2 h, and quenched with acetic acid. Ethyl acetate (50 mL) was added, the solution was washed with 10% sodium hydroxide and brine, and the organic layer was dried ($MgSO_4$).

Boc-Nα-methylarginine(Mtr)OMe was dissolved in 1:1 TFA/at 0° C., and stirred, with warming to RT for 2 h. When the reaction appeared complete as judged by TLC, the solvent was removed under reduced pressure. Trace TFA was removed by azeotroping with toluene. ES(+) MS m/e= 415.4 (M+H).

b) (2,2-Diphenylethoxn)acetyl-Nα-methylarginine(Mtr) OMe

To Nα-methylarginine(Mtr)OMe TFA salt (0.188 g, 0.36 mmol) in 2 mL of DMF was added DIEA (0.078 g, 0.60 mmol). Then a premixed solution of 2,2-diphenylethoxyacetic acid (0.100 g, 0.39 mmol), PyBOP (0.370 g, 0.71 mmol) and DIEA (0.196 g, 1.51 mmol) in 1 mL of DMF was added. The solution was stirred at RT overnight. Ethyl acetate was added, the solution was washed with 3N HCl, brine, $NaHCO_3$(sat'd), and brine again. The organic layer was dried ($MgSO_4$), filtered, and the solvent was removed under reduced pressure. Purification by silica gel chromatography (50% ethyl acetate/hexanes) yielded the title compound (86 mg). ES(+) MS m/e=653.3 (M+H).

c) (2,2-Diphenylethoxy)acetyl-Nα-methylarginine(Mtr)

To (2,2-diphenylethoxy)acetyl-Nα-methylarginine(Mtr) OMe was added 2 mL of THF and 2 mL of 1M LiOH. The solution was stirred at RT for 2.5 h, ethyl acetate was added, and the aqueous layer was acidified with 3N HCl. The organic layer was dried ($MgSO_4$), filtered, and the solvent was removed under reduced pressure. Purification by silica gel chromatography (0.1% AcOH/2% MeOW/$CH_2Cl_2$) yielded the title compound (40 mg). ES(+) MS m/e=639.2 (M+H).

d) (2,2-Diphenylethoxyacetyl-Nα-methylarginine

To (2,2-diphenylethoxy)acetyl-Nα-methylarginine(Mtr) (0.040 g, 0.06 mmol) was added 2 mL of a 2.5% TIPS in 1:1 $CH_2Cl_2$/TFA solution. The solution was stirred at RT for 4 h. The solvent was removed under reduced pressure, and the title compound was precipitated out of solution using diethyl ether. ES(+) MS m/e=427.3 (M+H).

EXAMPLE 7

Inhalant Formulation

A compound of Formula (I), (1 mg to 100 mg) is aerosolized from a metered dose inhaler to deliver the desired amount of drug per use.

EXAMPLE 8

| Tablet Formulation | |
|---|---|
| Tablets/Ingredients | Per Tablet |
| 1. Active ingredient (Cpd of Form. (I) | 40 mg |
| 2. Corn Starch | 20 mg |
| 3. Alginic acid | 20 mg |
| 4. Sodium Alginate | 20 mg |
| 5. Mg stearate | 1.3 mg |

Procedure for Tablet Formulation:

Ingredients 1, 2, 3 and 4 are blended in a suitable mixer/blender. Sufficient water is added portion-wise to the blend with careful mixing after each addition until the mass is of a consistency to permit its conversion to wet granules. The wet mass is converted to granules by passing it through an oscillating granulator using a No. 8 mesh (2.38 mm) screen. The wet granules are then dried in an oven at 140° F. (60° C.) until dry. The dry granules are lubricated with ingredient No. 5, and the lubricated granules are compressed on a suitable tablet press.

EXAMPLE 9

Parenteral Formulation

A pharmaceutical composition for parenteral administration is prepared by dissolving an appropriate amount of a compound of formula I in polyethylene glycol with heating. This solution is then diluted with water for injections (to 100 mL). The solution is then rendered sterile by filtration through a 0.22 micron membrane filter and sealed in sterile containers.

All publications, including but not limited to patents and patent applications cited in this specification are herein incorporated by reference as if each individual publication were specifically and individually indicated to be incorporated by reference as though fully set forth.

What is claimed is:

1. A compound according to Formula (I):

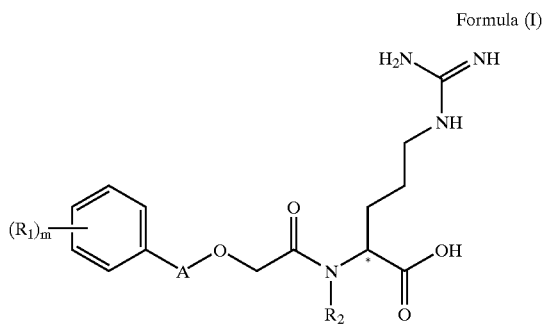

Formula (I)

wherein:
  A represents $C_{1-4}$ alkylene, unsubstituted or optionally substituted by $C_{1-4}$ alkyl or aryl; or
  A forms a 5–8 membered fused aliphatic ring with the adjacent phenyl ring;
  m is an integer from 1 to 3;
  each $R_1$ is independently selected form the group consisting of halo, $C_{1-4}$ alkyl, methanesulfonyl, alkoxy, nitrile, dimethylamine, methylenedioxy and $CF_3$; and
  $R_2$ is hydrogen or methyl.

2. A compound according to claim 1 wherein the asterisk*represents an S configuration.

3. A compound according to claim 2 wherein A is phenethyl.

4. A compound according to claim 3 wherein $R_1$ is hydrogen.

5. A compound according to claim 4 wherein m is 0.

6. A compound according to claim 1 selected from the group consisting of:
  1-[7-(4-hydroxyphenylmethyl)naphthyloxy]acetylarginine;
  (2,2-Diphenylethoxy)acetylarginine;
  (2,2-Diphenylethoxy)acetyl-Nα-methylarginine;
  (3-Chlorobenzyloxy)acetylarginine;
  2-Naphthyloxyacetylarginine;
  (2,3-Dimethylphenoxy)acetylarginine;
  8-(Quinolinyloxy)acetylarginine;
  6-(Quinolinyloxy)acetylarginine;
  2-(1-Bromonaphthyloxy)acetylarginine;
  (4-Benzyloxyphenoxy)acetylarginine; and
  2-(6-Methoxynaphthyloxy)acetylarginine.

7. A compound according to claim 6 selected from the group consisting of:
  1-[7-(4-hydroxyphenylmethyl)naphthyloxy]acetylarginine;
  (2,2-Diphenylethoxy)acetylarginine; and
  2-Naphthyloxyacetylarginine.

8. (2,2-Diphenylethoxy)acetylarginine.

9. A pharmaceutical composition comprising a compound of claim 1 and a pharmaceutically acceptable carrier.

10. A method of antagonizing a C3A receptor which comprises administering to a subject in need thereof, an effective amount of a compound of claim 1.

11. A method according to claim 10 wherein the compound is selected from the group consisting of:
  1-Naphthyloxyacetylarginine;
  1-[7-(4-hydroxyphenylmethyl)naphthyloxy]acetylarginine;
  (2,2-Diphenylethoxy)acetylarginine;
  (2,2-Diphenylethoxy)acetyl-Nα-methylarginine;
  (3-Chlorobenzyloxy)acetylarginine;
  2-Naphthyloxyacetylarginine;
  (2,3-Dimethylphenoxy)acetylarginine;
  8-(Quinolinyloxy)acetylarginine;
  6-(Quinolinyloxy)acetylarginine;
  2-(1-Bromonaphthyloxy)acetylarginine;
  (4-Benzyloxyphenoxy)acetylarginine; and
  2-(6-Methoxynaphthyloxy)acetylarginine.

12. A method of treating an immune or inflammatory disease or disorder characterized by abnormal levels of anaphylatoxins which comprises administering to a subject in need thereof an effective amount of a compound of claim 1.

13. A method according to claim 12 wherein the disease or disorder is selected from the group consisting of rheumatoid arthritis, Alzheimer's disease, psoriasis, gout, multiple sclerosis, systemic lupus erythematosus, glomerulonephritis and adult respiratory distress syndrome.

* * * * *